United States Patent [19]
Blaustein et al.

[11] Patent Number: 5,844,091
[45] Date of Patent: Dec. 1, 1998

[54] ANTIBODY HAVING BINDING SPECIFICITY FOR HUMAN OUABAIN

[75] Inventors: Mordecai P. Blaustein; John M. Hamlyn, both of Baltimore, Md.; Douglas W. Harris; James H. Ludens, both of Portage, Mich.; William Rodney Mathews, Plainwell, Mich.; Jed F. Fisher, Three Rivers, Mich.; Frederic Mandel, Vicksburg, Mich.; Donald W. DuCharme, Paw Paw, Mich.

[73] Assignee: University of Maryland, Baltimore, Baltimore, Md.

[21] Appl. No.: 81,693

[22] Filed: Jun. 25, 1993

Related U.S. Application Data

[62] Division of Ser. No. 921,207, Jul. 28, 1992, Pat. No. 5,429,928, which is a division of Ser. No. 575,714, Aug. 31, 1990, Pat. No. 5,164,296.

[51] Int. Cl.$^6$ ............................ C07K 16/18; C07K 14/47
[52] U.S. Cl. .................................. 530/387.1; 530/388.9; 530/389.8; 530/412; 530/344; 530/800; 530/807
[58] Field of Search .................................. 530/35, 387.1, 530/388.9, 389.8, 412, 344, 800, 807; 435/69.1; 935/12

[56] References Cited

U.S. PATENT DOCUMENTS

| | | |
|---|---|---|
| 4,551,426 | 11/1985 | Freytag et al. . |
| 4,665,019 | 5/1987 | Hamlyn et al. . |
| 4,772,684 | 9/1988 | Brunck et al. . |
| 4,780,314 | 10/1988 | Graves et al. . |

FOREIGN PATENT DOCUMENTS

| | | |
|---|---|---|
| 0381527 | 8/1990 | European Pat. Off. . |
| WO 8702588 | 5/1987 | WIPO . |

OTHER PUBLICATIONS

Paci A., et al J. Pharm. & Biomed. Analysis 14:983–988, 1996.
Deray et al, *Hypertension*, 8(7):632–638 (1986).
Smith, J. of Clin. Pharm., 25(7):522–528, 1985.
Wenger et al., J. of Amer. College of Cardiology, 5(5suppl. A):118–123, 1985.
Buchman et al, *Hybridoma*, 4(2):173–177 (1985).
Masugi et al., *Journal of Human Hypertension*, 2:17–20 (1988).
Smith, *J. Clin. Invest.*, 51:1583–1593 (1972).
Hamlyn et al, *Nature*, 305:646 (1983).
Gruber et al, *Nature*, 287:743–745 (1980).
Finegold et al, *Metabol. Clin. and Exp.*, 37:557–561 (1988) Abst. Only.
Clerico et al, *Clin. Physio. Biochem.*, 8:153–168 (1990) Abst. Only.
Biver, *Child Nephron. Neur.*, 10:164–180 (1990) Abst. Only.
Mathews, *Hypertension*, 17:923–929 (1991) Abst. Only.
Mathews, *Hypertension*, 17:930–935 (1991).
Hamlyn et al, *Am. J. Physiol.*, 251:F563–F575 (1986).
Goto et al, *Biochem. Biophys. Res. Comm.*, 152:322–327 (1988).
Tamura et al, *Biochem.*, 27:4244–4253 (1988).
Hamlyn et al, *Proc. Nat'l Acad. Sci. USA.*, 88:9907 (1991).
Kelly et al, *J. Biol. Chem.*, 260(21):11396–11405 (1985).
Hamlyn et al, *J. Hypertension.*, 13:681–689 (1989).
Hamlyn et al, *J. Biol. Chem.*, 264:7395–7404 (1989).
Masugi et al, *Clin. Exper. Hyperten.–Theory Pract.*, A9:1233–1242 (1987).
Masugi et al, *Biochem. Biophys. Res. Comm.*, 135(1):41–45 (1986.
Masugi et al, *J. Hypertension.*, 6(4):8351–8353 (1988).
Hamlyn et al, *Proc. Nat'l Acad. Sci. USA*, 88:6259–6263 (1991).
Correction of Hamlyn et al, *Proc. Nat'l Acad. Sci. USA*, 88:6259–6263 (1991).
Harris et al, *J. Hypertension*, 17:936–943 (1991).
Bova et al, *J. Hypertension*, 17:944–950 (1991).
Ludens et al, *J. Hypertension*, 17:923–929 (1991).
Editorial, *Lancet*, 338:543–544 (1991).
Goto et al, *Biochem. Biophys. Res. Comm.*, 154:847–853 (1988).
Goto et al, *Clin. Chem.*, 34:2392–2393 (1988).
Hamlyn et al, *Nature*, 300:650–652 (1982).
Haddy et al, *N. Engl. J. Med.*, 316:621–623 (1987).
Hamlyn et al, *J. Endocrinol.*, 122:409–420 (1989).
Maurer et al, *Meth. Enzymol.*, 70:49–70 (1980).
DiBartolo, V. et al 1995 Life Sciences 57(15: 1417–1425.

*Primary Examiner*—Toni R. Scheiner
*Assistant Examiner*—Nancy A. Johnson
*Attorney, Agent, or Firm*—Sughrue, Mion, Zinn, Macpeak & Seas, PLLC

[57] ABSTRACT

Methods for diagnosing pre-hypertension, hypertension, congestive cardiomyopathy, renal failure, salt-sensitivity and adenomas and endocrine cell hyperplasias are disclosed. Also disclosed are methods for monitoring hypertension therapy, congestive cardiomyopathy therapy, renal failure therapy and adenoma and endocrine cell hyperplasia therapy. These methods involve using an antibody having binding specificity to ouabain to immunologically measure the level of human ouabain in body fluid or tissue of a subject. Additionally, methods for treating a hypertensive subject by inducing passive or active immunity to human ouabain in the subject are disclosed, along with an antibody having binding specificity for ouabain.

10 Claims, No Drawings

ANTIBODY HAVING BINDING SPECIFICITY FOR HUMAN OUABAIN

This application is a Divisional of application Ser. No. 07/921,207, filed Jul. 28, 1992, now U.S. Pat. No. 5,429,928 which in turn is a Divisional of application Ser. No. 07/575,714, filed Aug. 31, 1990, now U.S. Pat. No. 5,164,296.

The development of the present invention was supported by the Upjohn Company and the University of Maryland at Baltimore.

FIELD OF THE INVENTION

The present invention relates to methods for diagnosing pre-hypertension, hypertension, congestive cardiomyopathy, renal failure, salt-sensitivity and adenomas and endocrine cell hyperplasias. The present invention also relates to methods for monitoring hypertension therapy, congestive cardiomyopathy therapy, renal failure therapy and adenoma and endocrine cell hyperplasia therapy. These methods involve using an antibody having binding specificity to ouabain to immunologically measure the level of human ouabain in body fluid or tissue of a subject. Additionally, the present invention relates to methods for treating a hypertensive subject by inducing passive or active immunity to human ouabain in the subject, and to an antibody having binding specificity for ouabain.

BACKGROUND OF THE INVENTION

I. Endogenous Factors

Endogenous factors include a group of factors found in animal and human body fluids and tissues. These factors appear to be associated with natriuresis, the excretion of sodium in the urine. Natriuresis arises as a result of inhibition of $(Na^++K^+)$ATPase (the biochemical equivalent of the sodium pump) by the endogenous factors. The sodium pump drives the transepithelial resorption of sodium in animal and human kidneys (De Wardener, H. E. et al, *Clin. Sci.,* 63:415–420 (1982)). However, $(Na^++K^+)$ATPase is not limited to kidney tissue. That is, this enzyme can be found in virtually all animal and human cells.

There is extensive literature on the isolation and purification of endogenous factors that inhibit $(Na^++K^+)$ATPase; the following is only a partial list: Gruber, K. A. et al, *Nature,* 287:743–745 (1980); Cloix, J. F. et al, *Biochem. Biophys. Res. Commun.,* 131:1234–1240 (1985); Kelly, R. A. et al, *J. Biol. Chem.,* 260:11396–11405 (1985); Fishman, M. C., *Proc. Natl. Acad. Sci. USA,* 76:4661–4663 (1979); Lichstein, D. et al, *Biochem. Biophys. Res. Commun.,* 96:1518–1523 (1980); Akagawa, K., *J. Neurochem.,* 42:775–780 (1984); Jandhyala, B. S. et al, *Clin. Sci.,* 70:103–110 (1986); Carilli, C. T. et al, *J. Biol. Chem.,* 260:1027–1031 (1985); Clarkson, E. et al, *Kidney Internatl.,* 16:710–721 (1979); Kramer, H. et al, *Hormonal Regulation of Sodium Excretion,* pp. 303–323 (1980); Cloix, J. F., *FEBS Lett.,* 176:223–228 (1984); de The, H. et al, *J. Cardiovas. Pharmacol.,* 6:549–554 (1984); Devynck, M. A. et al, *Clin. and Exper. Hyperten.— Theory and Pract.,* A6:441–453 (1984); and Tamura, M. et al, *J. Hyperten.,* 5:219–255 (1981).

One such factor or family of factors, i.e., endogenous digitalis-like factor or substance (hereinafter "EDLF" or "EDLS"), is believed to be natriuretic by virtue of its ability to inhibit $(Na^++K^+)$ ATPase.

EDLF inhibits $(Na^++K^+)$ATPase in at least three different biochemical assay systems (Hamlyn, J. M. et al, *J. Biol. Chem.* 264:7395–7404 (1989)). However, EDLF does not cross-react with antibodies raised against digoxin. In this regard, and in terms of chromatographic and kinetic properties, EDLF is different from some of the other previously isolated $(Na^++K^+)$ATPase inhibitors (Graves, S. W., *Ann. Int. Med.,* 99:604–608 (1983); Gruber, K. A. et al, *Nature,* 287:743–745 (1980); Gruber, K. A. et al, *Hyperten.,* 4:348–354 (1982); Vasdev, S. et al, *Res. Commun. Chem. Pathol. Pharmacol.,* 49:387–399 (1985); Kramer, H. J. et al, *Renal Physiol.,* 5:80–90 (1985); Kelly, R. A. et al, *J. Biol. Chem.,* 260:11396–11405 (1985); and Crabos, M. et al, *FEBS Lett.,* 176:223–228 (1984)).

In at least two instances, digitalis-like factors with chromatographic properties similar to EDLF have been described in bovine adrenal tissue (Tamura, M., *Biochem.,* 27:4244–4253 (1988)); and in human urine (Goto, A. et al, *Biochem. Biophys. Res. Commun.,* 152:322–327 (1988)). The estimated molecular weights, as determined by fast atom bombardment mass spectrometry, of these digitalis-like factors are 336 and 343 Daltons, respectively.

A digitalis-like factor has also been detected in human amniotic fluid (U.S. Pat. No. 4,780,314). The molecular weight of this factor is described as being 150–250 Daltons. In addition, this factor is taught to cross-react strongly with digoxin antibodies, is highly protein bound in plasma and is a substrate for catechol-o-methyl transferase (COMT). These properties distinguish this digitalis-like factor from the EDLF described in the present invention, which is of higher molecular weight, does not cross-react with digoxin antibodies (Hamlyn, J. M. et al, *J Biol. Chem.,* 264:7395–7404 (1989)), is not highly protein bound in plasma and is not a substrate for COMT.

II. The Role of EDLF in Hypertension

It has been suggested that EDLF may play a pathogenetic role in hypertension through inhibition of $(Na^++K^+)$ATPase in vascular smooth muscle (Blaustein, M. P., *Am. J. Physiol.,* 323:C165–C173 (1977)).

In established hypertension, the plasma levels of EDLF appear to be correlated with blood pressure (Hamlyn, J. M. et al, *Nature,* 300:650–562 (1982); and Hamlyn, J. M. et al, *J. Endocrinol.,* 122:409–420 (1989)). However, the levels of EDLF rise before the blood pressure does, as a result of volume expansion (Hamlyn, J. M., *J. Endocrinol.,* 122:409–420 (1989)). The elevated levels of EDLF may therefore be used as a predictor of hypertension because EDLF increases vascular smooth muscle contractility, and thus apparently causes the elevation of the blood pressure (Blaustein, M. P., *Am. J. Physiol.,* 232:C165–C173 (1977); and Blaustein, M. P. et al, *Japan. J. Hyperten.,* 11:107–117 (1989)).

Several types of hypertension, including essential hypertension, adrenocorticoid-induced hypertension (including primary aldosteronism) and pregnancy-induced hypertension, are the consequence of excessive sodium retention by the body. Initially, the salt (sodium and chloride) retention is manifested as an expansion of plasma volume (Hamlyn, J. M. et al, *Am. J. Physiol.,* 251:F563–F575 (1986)). This expansion of plasma volume, if chronic, is sufficient to cause the elevation of blood pressure through an increase in vascular smooth muscle contractility and consequent increase in peripheral vascular resistance (Guyton, A. C. et al, *Am. J. Med.,* 52:584–594 (1972)). The volume expansion appears to promote the secretion of an EDLF that has been extracted from the plasma of volume-expanded humans and purified by dialysis of human plasma, lyophilization of the dialysate, extraction of methanol-soluble components, and flash evaporation followed by preparative, semi-preparative and analytical scale reverse phase chromatography. The resulting purified EDLF differs from the plant steroid ouabain (molecular weight of 585 Daltons) in that the rate of loss of inhibitory activity over the course of time in an environment of 6.0N HCl at 110° C. is significantly greater for the purified EDLF than for ouabain. Further, under type II-phosphorylating conditions, this EDLF interacts with (Na$^+$+K$^+$)ATPase with an affinity between 12–25 fold higher than that of ouabain (Hamlyn, J. M. et al, *J. Biol. Chem.*, 264, 7395–7404 (1989); and Hamlyn, J. M. et al, *Hyperten.*, 13:681–689 (1989)). Thus, EDLF was not believed to be the plant steroid ouabain.

Moreover, the above-described purification procedures were subsequently found by Applicants to produce an insufficient quantity of EDLF (<1.0 μg) to carry out structural analysis. Further, attempts to scale up the procedure to produce a sufficient quantity of EDLF (at least 10 μg) failed because of the tendency of the preparative column to become completely blocked by the sample, resulting in a low yield. In addition, as a result of subsequent work (see Example 1 below), Applicants discovered that the EDLF purified by the above-described procedures was not homogeneous, as had been reported.

III. Identification of EDLF

A. Misidentification of EDLF

Antibodies against the plant steroid ouabain conjugated to bovine serum albumin (hereinafter "BSA") have been raised and shown to be able to detect elevated levels of an unknown factor with "ouabain-like immunoreactivity" in the plasma of subjects with primary aldosteronism (Masugi, F., *Biochem. Biophys. Res. Comm.*, 135:41–45 (1986)) and in the plasma of subjects with essential hypertension (Masugi, F., *Clin. Exper. Hyperten.—Theory Pract.*, A9:1233–1242 (1987)). This "ouabain-like immunoreactivity" was partially purified, and was found to be an "unstable lipid", possibly "an unstable peroxide . . . of low molecular weight" (Masugi, F., *J. Hyperten.*, 6:S351–S353 (1988)). Thus, the substance partially purified is not ouabain because ouabain is a steroid, not a lipid. Moreover, the results indicate that the anti-ouabain antibody employed is not highly specific for ouabain, and cross-reacts with substances in plasma other than cardenolides, i.e., lipids, that may inhibit (Na$^+$+K$^+$) ATPase. Thus, this antibody and assay method is not sufficiently selective, and therefore is not suitable for detection of the EDLF that appears to elevate blood pressure in hypertensive subjects.

None of the other factors isolated to date have been reported to cross-react with antibodies raised against ouabain. In fact, it has been demonstrated that the previously isolated factors do not cross-react with antibodies having binding specificity for ouabain (Kelly, R. A., *J. Biol. Chem.*, 260:11396–11405 (1985)).

B. Correct Identification of EDLF

Using a newly developed procedure (see Example 1 below), Applicants have, for the first time in the present invention, been able to isolate and purify EDLF so as to identify such. This new procedure involves the use of hydrophobic chromatography employing an amberlite XAD-2 resin so as to enrich for EDLF prior to preparative chromatography, and then the use of affinity chromatography employing (Na$^+$+K$^+$)ATPase as the ligand. This type of affinity chromatography could not have been used to isolate and purify the EDLF described by Hamlyn, J. M. et al, *J. Biol. Chem.*, 264:7395–7404 (1989) and Hamlyn, J. M. et al, *Hyperten.*, 13:681–689 (1989) because of the presence of numerous impurities which interact non-selectively with (Na$^+$+K$^+$)ATPase. Because of this non-selective interaction, (Na$^+$+K$^+$)ATPase was unable to bind EDLF with high affinity.

The present invention is based upon the discovery by Applicants, in the present invention, that EDLF is unique in that it cross-reacts 100% (within experimental error) with antibodies having binding specificity for ouabain. Applicants have also purified EDLF to homogeneity in the present invention and have discovered that EDLF is indistinguishable from plant ouabain in terms of fast atom bombardment mass spectroscopy and biological properties; EDLF is thus a human ouabain. Ouabain heretofore was only thought to exist in plants.

It is believed, in the present invention, that human ouabain, at elevated levels, inhibits (Na$^+$+K$^+$)ATPase in a variety of cells, including vascular smooth muscle cells and neurons, including sympathetic neurons, that activate vascular smooth muscle. Inhibition of (Na$^+$+K$^+$)ATPase is believed to raise intracellular sodium in various cell types and lead to a secondary rise in intracellular calcium via sodium/calcium exchange (Bova, S. et al, *Am. J. Physiol.*, 259:H409–H423 (1990)). The increased availability of intracellular calcium in the arterial smooth muscle cells is believed to enhance contractility (Blaustein, M. P. et al, *Ann. N.Y. Acad. Sci.*, 488:199–216 (1986); Woolfson, R. et al, *Hyperten.*, 15:583–590 (1990); and Bova, S. et al, *Am. J. Physiol.*, 259:H409–H423 (1990)), and eventually lead to a rise in blood pressure, when the ability of the cardiovascular reflexes to control blood pressure is exceeded (Blaustein, M. P., *Am. J. Physiol.*, 232:C165–173 (1977); and Blaustein, M. P. et al, *Japan. J. Hyperten.*, 11:107–117 (1989)).

IV. Pre-Hypertension

Studies in pigs have suggested that EDLF may be increased immediately prior to the development of hypertension, i.e., at the pre-hypertensive phase (Hamlyn, J. M., *J. Endocrin.*, 122:409–420 (1989)). Thus, the presence of elevated levels of human ouabain in normotensive subjects is believed, in the present invention, to be indicative of the pre-hypertensive state and to represent a valuable indicator of future risk for development of hypertension.

V. White-Coat Hypertension

Some individuals have elevated levels of blood pressure, e.g., diastolic blood pressure about 90 to 104 mm Hg, on repeated visits to the physician's office, but normal blood pressure during ambulatory monitoring (Pickering, T. G. et al, *J. Am. Med. Assn.*, 259:225–228 (1988); and Rucker, L. et al, *South. Med. J.*, 83:610–612 (1990)). The presence of normal levels of human ouabain in these subjects with high blood pressure is believed, in the present invention, to be indicative of "white-coat hypertension" or a pseudo-hypertensive state, and thus a valuable indication of subjects who do not need therapy for hypertension.

VI. Congestive Cardiomyopathy

Various types of cardiac dysfunction (cardiomyopathies) are associated with disturbances in the relationship between blood volume and arterial blood pressure. Examples of such cardiomyopathies include ischemic heart disease, familial cardiomyopathy, alcoholic cardiomyopathy, peripartum cardiomyopathy, endocardial fibroelastosis, postcarditic cardiomyopathy, hypertensive cardiomyopathy, idiopathic cardiomyopathy, and various secondary forms of myocardial involvement, e.g., in connective tissue diseases and neuromuscular diseases, such as muscular dystrophy.

In instances where the cardiomyopathy involves hypocontractility of the left or right heart or both, more blood returns to the heart via the venous system than can be pumped away. The accumulation of fluid (salt and water) leads to congestion of the lungs and/or venous system. The usual therapeutic regimen for cardiomyopathies consists of diuretics, sodium restriction and digitalis (digoxin) (Glick, G. et al, In: *Harrision's Principles of Internal Medicine*, 9th Ed., eds. Isselbacher, K. et al, McGraw Hill, New York, pp. 1141–1146 (1980)). It has been suggested that part of the rationale for the effectiveness of digitalis in cardiomyopathy arises because this therapeutic agent compensates for the absence or reduced levels (below normal) of an endogenous digitalis (Szent-Gyorgyi, A., In: *Chemical Physiology of Contraction in Body and Heart Muscle*, Academic Press, New York, pp. 86–91 (1953)). Thus, absence or reduced levels of human ouabain is believed, in the present invention, to be indicative of future risk for developing congestive cardiomyopathy in otherwise normal subjects. In addition, reduced levels of human ouabain in those subjects with congestive failure is believed, in the present invention, to identify those subjects within this group who are most likely to benefit from instigation of therapy using agents, such as digoxin and perhaps even human ouabain.

VII. Renal Failure

The kidney is responsible for the daily metabolism and "clearance" of a large variety of compounds from the body. It is known that when ouabain is administered to a subject, the excretory function of the kidney accounts for removal of 50–80% of the amount of administered ouabain (Selden, R. et al, *J. Pharmacol. Exp. Ther.*, 188:615–623 (1974); Lahrty, H. et al, *Pharmacol. Clinica*, 1:114–118 (1969); and Strobach, H. et al, *Naunyn-Schmeideberg's Arch. Pharmacol.*, 334:496–500 (1986)). Thus, alterations in renal excretory function for human ouabain are believed, in the present invention, to be detectable by changes in the levels of human ouabain. For example, a decrease in renal clearance of human ouabain is believed, in the present invention, to elevate levels of human ouabain. Moreover, the degree to which levels of human ouabain are elevated is believed, in the present invention, to be proportional to the degree of renal impairment. Thus, detection of an elevated level of human ouabain is believed, in the present invention, to be indicative of those subjects with renal disease (indicated by above-normal levels of serum creatinine) who may already have low-grade renal disease or who may be at risk for future development of renal failure.

Patients with chronic renal failure are dependent upon dialysis for the removal of unwanted or excess levels of a variety of compounds in the circulation. The efficacy of dialysis can be monitored by measuring serum creatinine and other indicators, such as blood urea nitrogen and plasma potassium. Measurement of human ouabain is believed, in the present invention, to also represent a useful indicator of the efficacy of dialysis in these patients. The level of human ouabain following dialysis and the rate at which the level of human ouabain is elevated between dialysis are believed, in the present invention, to be indicative of the severity of renal failure and the rate at which disease may progress to complete renal failure.

VIII. Salt-Sensitivity

Salt-sensitivity has been defined as a significant increase in blood pressure when a subject has an increased dietary intake of sodium from low (about 40 to 60 meq/24 hr) to high (about 200 to 250 meq/24 hr). In contrast, the blood pressure of salt-insensitive persons does not change significantly with similar manipulations of dietary sodium intake (Kawasaki, T. et al, *Am. J. Med.*, 64:193–198 (1978)).

Elevated levels of EDLF have been found in animal models of hypertension associated with sodium and water retention (Hamlyn, J. M., *J. Endocrin.*, 122:409–420 (1989); and see Example 4 below). Based upon these observations, it is believed, in the present invention, that levels of human ouabain in normotensive individuals are different in those individuals who are salt-sensitive. Salt-sensitive individuals are believed, in the present invention, to have elevated levels of human ouabain because of the tendency of blood volume to be greater in these individuals at all levels of sodium intake. Thus, measurement of a 24-hr urinary sodium level (as an indicator of daily dietary sodium ingestion) when coupled with measurements of human ouabain is believed, in the present invention, to be indicative of the presence of salt-sensitivity. A salt-sensitive subject is believed, in the present invention, to have a significantly greater increase in the level of human ouabain than salt-insensitive subjects when the dietary sodium intake is increased from a low-salt to a high-salt diet.

The ability to define salt-sensitive subjects in the normotensive (pre-hypertensive) population is useful in the recommendation of dietary and other therapeutic interventions which may prevent the future development of hypertension in these susceptible subjects. In addition, the ability to diagnose salt-sensitivity in hypertensive subjects should be similarly useful as an indicator of the response to different classes of anti-hypertensive agents. For example, salt-sensitive hypertensive subjects with elevated levels of human ouabain would be expected to show a better anti-hypertensive response to diuretic agents than other types of anti-hypertensive agents which do not act directly on blood volume.

IX. Adenomas and Endocrine Cell Hyperplasias

Adenomas are endocrine cell tumors, and endocrine cell hyperplasias refer to non-tumorous proliferation of these cells.

The secretion of human ouabain is believed, in the present invention, to be elevated when the endocrine cells involved in the biosynthesis of human ouabain become tumorous (adenomas) and oversecrete human ouabain. Similarly, hyperplasia of the endocrine cells involved in the biosynthesis of human ouabain will lead to increased production and secretion of human ouabain.

In addition, the level of human ouabain is believed, in the present invention, to be elevated in disorders associated with overproduction of a variety of steroids which share the same clearance mechanism as human ouabain in the kidney. These disorders include adenomas, such as ovarian, adrenal, pituitary and testicular adenomas and endocrine cell hyperplasias. Thus, the detection of elevated levels of human ouabain is believed, in the present invention, to indicate the existence of one or more of these disorders.

Furthermore, the levels of human ouabain are believed, in the present invention, to be a useful indicator of the response of adenomas and endocrine cell hyperplasias to therapeutic agents and/or surgical intervention.

SUMMARY OF THE INVENTION

An object of the present invention is to provide a method for diagnosing pre-hypertension.

A further object of the present invention is to provide a method for diagnosing hypertension.

An additional object of the present invention is to provide a method for diagnosing white-coat hypertension.

Another object of the present invention is to provide a method for determining subjects at risk to develop congestive cardiomyopathy.

Still another object of the present invention is to provide a method for determining subjects at risk to develop renal failure.

Yet another object of the present invention is to provide a method for determining the salt-sensitivity of subjects at risk to develop hypertension and hypertensive subjects.

A further object of the present invention is to provide a method for diagnosing adenomas or endocrine cell hyperplasias.

An additional object of the present invention is to provide a method for monitoring hypertensive therapy.

Another object of the present invention is to provide a method for monitoring congestive cardiomyopathy therapy.

Still another object of the present invention is to provide a method for monitoring renal failure therapy.

Yet another object of the present invention is to provide a method for monitoring adenoma and endocrine cell hyperplasia therapy.

A further object of the present invention is to provide a method for treating hypertensive subjects by inducing passive immunity to ouabain.

An additional object of the present invention is to provide a method for treating hypertensive subjects by inducing active immunity to ouabain.

Another object of the present invention is to provide an antibody having binding specificity for ouabain.

In a first embodiment, the above-described objects of the present invention have been met by a method for diagnosing pre-hypertension comprising the steps of:

(1) obtaining a body fluid or tissue sample from a subject with normal blood pressure;

(2) enriching the resulting body fluid or tissue sample obtained in step (1) for human ouabain;

(3) using an antibody having binding specificity for ouabain, immunologically measuring the level of human ouabain in the resulting enriched body fluid or tissue sample of step (2); and (4) comparing the level of human ouabain obtained in step (3) with an ouabain standard so as to detect a normal or elevated level of human ouabain in the subject and to diagnose the absence or presence of pre-hypertension, respectively.

In a second embodiment, the above-described objects of the present invention have been met by a method for diagnosing hypertension comprising the steps of:

(1) obtaining a body fluid or tissue sample from a subject with high blood pressure;

(2) enriching the resulting body fluid or tissue sample obtained in step (1) for human ouabain;

(3) using an antibody having binding specificity for ouabain, immunologically measuring the level of human ouabain in the resulting enriched body fluid or tissue sample of step (2); and (4) comparing the level of human ouabain obtained in step (3) with an ouabain standard so as to detect a normal or elevated level of human ouabain in the subject and to diagnose the absence or presence of hypertension, respectively.

In a third embodiment of the present invention, the above-described objects have been met by a method for diagnosing white-coat hypertension comprising the steps of:

(1) obtaining a body fluid or tissue sample from a subject with high blood pressure;

(2) enriching the resulting body fluid or tissue sample obtained in step (1) for human ouabain;

(3) using an antibody having binding specificity for ouabain, immunologically measuring the level of human ouabain in the resulting enriched body fluid or tissue sample of step (2); and (4) comparing the level of human ouabain obtained in step (3) with an ouabain standard so as to detect a normal or elevated level of human ouabain in the subject and to diagnose the presence or absence of white-coat hypertension, respectively.

In a fourth embodiment of the present invention, the above-described objects have been met by a method for determining subjects at risk to develop congestive cardiomyopathy comprising the steps of:

(1) obtaining a body fluid or tissue sample from a subject with cardiomyopathy;

(2) enriching the resulting body fluid or tissue sample obtained in step (1) for human ouabain;

(3) using an antibody having binding specificity for ouabain, immunologically measuring the level of human ouabain in the resulting enriched body fluid or tissue sample of step (2); and (4) comparing the level of human ouabain measured in step (3) with a ouabain standard so as to detect a normal or reduced level of human ouabain in the subject and to diagnose the absence or presence of the risk of developing congestive cardiomyopathy, respectively.

In a fifth embodiment of the present invention, the above-described objects have been met by a method for determining subjects at risk to develop renal failure comprising the steps of:

(1) obtaining a body fluid or tissue sample from a subject with renal disease;

(2) enriching the resulting body fluid or tissue sample obtained in step (1) for human ouabain;

(3) using an antibody having binding specificity for ouabain, immunologically measuring the level of human ouabain in the resulting enriched body fluid or tissue sample of step (2); and (4) comparing the level measured in (3) with an ouabain standard so as to detect a normal or elevated level of human ouabain in the subject and to diagnose the absence or presence of the risk of developing renal failure, respectively.

In a sixth embodiment of the present invention, the above-described objects have been met by a method for determining the salt-sensitivity of a subject at risk to develop hypertension or a hypertensive subject comprising:

(1) obtaining a body fluid or tissue sample from a subject at risk to develop hypertension or a hypertensive subject, respectively;

(2) enriching the resulting body fluid or tissue sample obtained in step (1) for human ouabain;

(3) using an antibody having binding specificity for ouabain, immunologically measuring the level of human ouabain in the resulting enriched body fluid or tissue sample of step (2);

(4) comparing the level of human ouabain measured in step (3) with an ouabain standard so as to detect a normal or elevated level of human ouabain in the subject; and (5) repeating steps (1)–(4) at suitable time intervals after the initiation of a low-salt or high-salt diet and measuring the level of human ouabain at each time interval so as to determine the salt-sensitivity of said subject, wherein when the level of human ouabain is elevated and the elevated level of human ouabain is due to a change from a low-salt to a high-salt diet, such is indicative of salt-sensitivity.

In a seventh embodiment of the present invention, the above-described objects have been met by a method for diagnosing adenomas or endocrine cell hyperplasias comprising the steps of:

(1) obtaining a body fluid or tissue sample from a subject;
(2) enriching the resulting body fluid or tissue sample obtained in step (1) for human ouabain;
(3) using an antibody having binding specificity for ouabain, immunologically measuring the level of human ouabain in the resulting enriched body fluid or tissue sample of step (2);
(4) comparing the level of human ouabain measured in step (3) with an ouabain standard so as to detect a normal or elevated level of human ouabain in the subject; and
(5) repeating steps (1)–(4) at suitable time intervals after the initiation of a low-salt or high-salt diet and measuring the level of human ouabain at each time interval so as to determine the presence of adenomas or endocrine cell hyperplasias in said subject, wherein when the level of human ouabain is elevated and the elevated level of human ouabain is not due to a change from a low-salt to a high-salt diet, such is indicative of adenomas or hyperplasias.

In an eighth embodiment, the above-described objects of the present invention have been met by a method for monitoring hypertension therapy comprising the steps of:
(1) obtaining a body fluid or tissue sample from a subject diagnosed as afflicted with hypertension;
(2) enriching the resulting body fluid or tissue samples obtained in step (1) for human ouabain;
(3) using an antibody having binding specificity for ouabain, immunologically measuring the level of human ouabain in the resulting enriched body fluid or tissue sample of step (2); and
(4) repeating steps (1)–(3) at suitable time intervals after the initiation of hypertension therapy and measuring the level of human ouabain at each time interval so as to monitor the effect of said hypertension therapy, wherein a reduced level of human ouabain over the course of hypertension therapy is indicative of effective hypertension therapy.

In a ninth embodiment, the above-described objects of the present invention have been met by a method for monitoring congestive cardiomyopathy therapy comprising the steps of:
(1) obtaining a body fluid or tissue sample from a subject diagnosed as afflicted with congestive cardiomyopathy;
(2) enriching the resulting body fluid or tissue sample obtained in step (1) for human ouabain;
(3) using an antibody having binding specificity for ouabain, immunologically measuring the level of human ouabain in the resulting enriched body fluid or tissue sample of step (2); and
(4) repeating steps (1)–(3) at suitable time intervals after the initiation of congestive cardiomyopathy therapy and measuring the level of human ouabain at each time interval so as to monitor the effect of said congestive cardiomyopathy therapy, wherein an increasing level of human ouabain over the course of congestive cardiomyopathy therapy is indicative of effective congestive cardiomyopathy therapy.

In a tenth embodiment, the above-described objects of the present invention have been met by a method for monitoring renal failure therapy comprising the steps of:
(1) obtaining a body fluid or tissue sample from a subject diagnosed as afflicted with renal failure;
(2) enriching the resulting body fluid or tissue sample obtained in step (1) for human ouabain;
(3) using an antibody having binding specificity for ouabain, immunologically measuring the level of human ouabain in the resulting enriched body fluid or tissue sample of step (2); and
(4) repeating steps (1)–(3) at suitable time intervals after the initiation of renal failure therapy and measuring the level of human ouabain at each time interval so as to monitor the effect of said renal failure therapy, wherein a decreasing level of human ouabain over the course of renal failure therapy is indicative of effective renal failure therapy.

In an eleventh embodiment, the above-described objects of the present invention have been met by a method for monitoring adenoma or endocrine cell hyperplasia therapy comprising the steps of:
(1) obtaining a body fluid or tissue sample from a subject diagnosed as afflicted with adenomas or endocrine cell hyperplasias;
(2) enriching the resulting body fluid or tissues sample obtained in step (1) for human ouabain;
(3) using an antibody having binding specificity for ouabain, immunologically measuring the level of human ouabain in the resulting enriched body fluid or tissue sample of step (2); and
(4) repeating steps (1)–(3) at suitable time intervals after the initiation of adenoma or endocrine cell hyperplasia therapy and measuring the level of human ouabain at each time interval so as to monitor the effect of said adenoma or endocrine cell hyperplasia therapy, wherein a decreasing level of human ouabain over the course of adenoma or endocrine cell hyperplasia therapy is indicative of effective adenoma or endocrine cell hyperplasia therapy.

In a twelfth embodiment of the present invention, the above-described objects have been met by a method for treating hypertensive subjects comprising administering to a hypertensive subject a therapeutically effective amount of an antibody having binding specificity for ouabain so as to induce passive immunity to human ouabain in said subject.

In a thirteenth embodiment of the present invention, the above-described objects have been met by a method for treating hypertensive subjects comprising administering to a hypertensive subject a therapeutically effective amount of conjugates of ouabain so as to induce active immunity to human ouabain in said subject.

In a fourteenth embodiment of the present invention, the above-described objects have been met by an antibody having binding specificity for ouabain.

DETAILED DESCRIPTION OF THE INVENTION

As used herein, "pre-hypertension" means the presence of an elevated level of human ouabain, but a normal level of blood pressure.

Normal blood pressure varies depending upon the age, height, weight, sex and race of the subject. Other factors include risks such as smoking, heredity and alcohol. Generally, normal blood pressure is considered to range from about 105/60 to 140/90 mm Hg, and typically is about 120/80 mm Hg. Thus, a high (borderline) normal blood pressure would be greater than about 130/85 to less than about 140/90 mm Hg. Further, a high (above normal) blood pressure would be greater than about 140/90 mm Hg.

As used herein, "hypertension" means the presence of an elevated level of human ouabain and an elevated level of blood pressure, i.e., above normal blood pressure.

Examples of hypertension include essential hypertension, adrenocorticoid-induced hypertension, pregnancy-induced hypertension, renal hypertension and pheochromocytoma.

As used herein, "white-coat hypertension" means the presence of a normal level of human ouabain and an elevated level of blood pressure, i.e., above normal blood pressure.

As used herein, "at risk to develop congestive cardiomyopathy" means the presence of a reduced level of human ouabain and cardiomyopathy.

As used herein, "cardiomyopathy" means diseases due to dysfunction of the myocardium or cardiac muscle.

Examples of cardiomyopathy include ischemic heart disease, familial cardiomyopathy, alcoholic cardiomyopathy, peripartum cardiomyopathy, endocardial fibroelastosis, postcarditic cardiomyopathy, hypertensive cardiomyopathy, idiopathic cardiomyopathy, and various secondary forms of myocardial involvement, e.g., in connective tissue diseases and neuromuscular diseases, such as muscular dystrophy.

As used herein, "at risk to develop renal failure" means the presence of an elevated level of human ouabain and renal disease.

As used herein, "renal disease" means diseases associated with destruction of renal mass.

Examples of renal disease include glomerulonephritis, diabetic nephropathy, tubulointerstital disease, polycystic renal disease and nephrosclerosis. Elevated levels of serum creatinine, and perhaps also elevated levels of blood urea nitrogen, are known to be early signs of renal disease (Coe, F. L., In: *Harrision's Principles of Internal Medicine,* 9th Ed., eds. Isselbacher, K. et al, McGraw Hill, New York, pp. 215–219 (1980)).

As used herein "salt-sensitivity" means an elevated level of human ouabain as a result of a change from a low-salt to a high-salt diet.

Examples of "subjects at risk to develop hypertension" include those subjects who have one or both parents that are hypertensive, overweight subjects, and subjects with high normal blood pressure and subjects with renal disease.

As used herein "hypertensive subject" means a subject diagnosed as afflicted with hypertension.

As used herein "adenomas or endocrine cell hyperplasias" means an elevated level of human ouabain which is not a result of a change from a low-salt to a high-salt diet.

As used herein, "adenomas" refer to endocrine cell tumors, and "endocrine cell hyperplasias" refer to non-tumorous proliferation of these cells.

The adenomas and endocrine cell hyperplasias include ovarian, adrenal, pituitary or testicular adenomas and endocrine cell hyperplasias, as well as adenomas and hyperplasias of human ouabain secreting endocrine cells.

A "low-salt diet" means an intake of about 60 meq of sodium per day or less, generally about 40 to 60 meq of sodium per day.

A "high-salt diet" means an intake of about 200 meg of sodium per day or greater, generally about 200 to 250 meg of sodium per day.

Whether or not a "low-salt diet" or a "high-salt diet" is being effected can be determined by measuring the daily urinary sodium excretion from said subject. This is because essentially all of the daily salt intake is excreted as sodium in the urine over a period of 24 hr. The daily urinary sodium excretion from said subject is determined by collecting a 24-hr urine specimen, measuring the total volume of the urine specimen, measuring the sodium concentration in an aliquot of the urine specimen using conventional flame photometry techniques, and multiplying the concentration in the aliquot by the total volume of the 24-hr urine specimen (MacGregor, G. A et al, Lancet, I:351–355 (1982)).

The level of human ouabain in a healthy subject, i.e., one not afflicted with pre-hypertension or hypertension, salt-sensitivity, cardiomyopathy, renal failure, adenomas or endocrine cell hyperplasias, will vary depending upon the body fluid and tissue which is obtained in step (1), and the age, weight, sex and race of the subject. Generally, a healthy subject has about 100 to 600 pmoles of human ouabain, more particularly, about 40 to 95 pmol/liter of human ouabain in its plasma, about 95 to 600 pmol/liter of human ouabain in its urine, and about 10,000 to 30,000 pmol/kg of human ouabain in its adrenal tissue.

The level of human ouabain in the plasma of a pre-hypertensive subject, hypertensive subject, a subject afflicted with congestive cardiomyopathy, a subject afflicted with renal failure and a subject afflicted with adenomas and endocrine cell hyperplasias will vary depending on the age, weight, sex, and race of the subject.

The level of human ouabain in the plasma of a pre-hypertensive subject is generally about 100 to 4000 pmol/liter.

The level of human ouabain in the plasma of a hypertensive subject is generally about 250 to 2000 pmol/liter.

The level of human ouabain in the plasma of a subject at risk to develop congestive cardiomyopathy is generally about 10 to 35 pmol/liter.

The level of human ouabain in the plasma of a subject at risk to develop renal failure is generally about 100 to 4000 pmol/liter.

In subjects at risk to develop hypertension, salt-sensitive subjects may have about a 2-fold or greater increase of human ouabain, typically a 2 to 7-fold increase of human ouabain, whereas salt-insensitive subjects may have less than a 2-fold increase in human ouabain, when the dietary sodium intake is increased from a low-salt to a high-salt diet.

Alternatively, particularly in hypertensive subjects, who have elevated levels of human ouabain even on a low-salt diet, salt-sensitive subjects may have more than a 150 pmol/liter rise in the plasma level of human ouabain, typically a 150 to 400 pmol/liter rise in the plasma level of human ouabain (generally a rise to a final level of about 250 to 2000 pmol/liter of plasma), whereas salt-insensitive subjects may have less than a 150 pmol/liter rise in the plasma level of human ouabain, when the dietary sodium intake is increased from a low-salt to a high-salt diet.

The level of human ouabain in the plasma of a subject afflicted with adenomas or endocrine cell hyperplasias is generally about 100 to 4000 pmol/liter.

The body fluid obtained in step (1) is not critical to the present invention. Examples of the body fluid include plasma, cerebrospinal fluid, saliva, semen, sweat, urine and amniotic fluid. Plasma is the preferred body fluid to be tested in the present invention because it is the most convenient.

The tissue sample obtained in step (1) is not critical to the present invention. Examples of the tissue samples include adrenal tissue, red blood cells, lymphocytes, and platelets. Red blood cells are the preferred tissue sample to be tested in the present invention.

It is preferable to employ body fluid in step (1) because the biological significance of human ouabain most likely arises from its presence in plasma, serum, etc.

The enrichment technique employed in step (2) is not critical to the present invention.

The body fluid can be enriched for human ouabain by a solid phase method as described in Example 3 below. Other methods of enrichment involving, for example, ultrafiltration, affinity chromatography, column chromatography, trichloracetic acid, perchloric acid, and ammonium sulfate, may be used. The solid phase method described in Example 3 below to enrich plasma is the preferred method. In this procedure, polar compounds, such as human ouabain, which interact with the solid phase column, are separated from the bulk protein and salts. These latter materials would otherwise interfere with the antibody reaction. When the bulk protein and salts have been washed through the column, human ouabain is preferentially eluted by washing with 25% (v/v) acetonitrile. The acetonitrile wash is dried under vacuum, and resuspended in assay buffer comprising 50 mM sodium phosphate buffer (pH 7.4) containing 0.08% (w/v) NaCl, 0.5% (v/v) Tween 20, 11.4 mg/l thimerosal and 10 mg/ml of BSA (hereinafter "assay buffer") for use with the antibody having binding specificity for ouabain. The use of 25% (v/v) acetonitrile for removing human ouabain from the column does not cause the elution of lipids from the column. Serum lipids are known to cause false positive reactions with antibodies directed against cardiac glycosides (Kelly, R. A. et al, *J. Biol. Chem.*, 250:11396–11405 (1985); and Masugi, F., *J. Hyperten.*, 6:S351–S353 (1988)). The enrichment protocol, therefore, constitutes a critical advantage in the selective measurement of human ouabain using antibodies having binding specificity for ouabain and distinguishes the present invention from previous measurements of ouabain-like immunoreactivity in plasma (Masugi, F., *Biochem. Biophys. Res. Commun.*, 135:41–45 (1986); and Masugi, F., *Clin. Exper. Hyperten.—Theory Pract.*, A9:1233–1242 (1987)).

The tissue sample can be enriched by homogenizing it in 10 parts of methanol and centrifuging so as to obtain a high speed supernatant. The supernatant is dried under vacuum and the residue thoroughly reconstituted in 10 parts of water containing 0.1% (w/v) trifluoroacetic acid (hereinafter "TFA"). Insoluble matter is removed by centrifugation and the supernatant applied to, e.g., a $C_{18}$ disposable column, as described for plasma in Example 3 below.

As used herein, "an antibody having binding specificity for ouabain" means an antibody which has:

(1) high affinity for ouabain, i.e., a dissociation constant on the order of about 7.0 nM or less of ouabain, generally about 0.5 to 7.0 nM of ouabain, typically about 5.0 nM of ouabain; and (2) low cross-reactivity for the well-known steroids present in human plasma, i.e., on the order of about 1.0% or less cross-reactivity, typically about 0.02 to 0.001% cross-reactivity.

The antibody can be polyclonal or monoclonal in nature. Polyclonal antibodies can be reproducibly prepared as described in Example 2 below.

The antibody of the present invention differs from the known antibodies which have been raised against ouabain due to the nature of the ouabain conjugates used to prepare the antibodies. That is, high antibody titers (>$10^6$) are obtained by employing sequential immunization and boosts with Antigens 1, 2 and 3 described in Example 2 below. These antigens were used so as to direct the immunological response to ouabain and not to the conjugate or the linker. This ensured the production of an antibody highly specific to ouabain. Previous attempts to raise ouabain antibodies have used only a single conjugate of ouabain and BSA for initial immunization and subsequent boosters (Smith, T., *J. Clin. Invest.*, 51:1583–1593 (1972); and Masugi, F., *Biochem. Biophys. Res. Commun.*, 135:41–45 (1986)).

The level of human ouabain in the extracted body fluid or tissue sample is immunologically measured using any conventional immunological technique, such as enzyme-linked immunosorbent assay (hereinafter "ELISA") or radioimmunoassay (hereinafter "RIA") (Chard, T., *An Introduction to Radioimmunoassay and Related Techniques*, Elsevier, Amsterdam (1987)). An ELISA is the preferred immunological technique when rapid results with large numbers of samples may be desired, although an RIA may be preferred for high precision measurements.

It should be apparent to one skilled in the art that the assay conditions set forth in Example 3 are preferred to optimize the assay for sensitivity and minimize the errors that may result from the assay of body fluids and tissue samples of slightly varying composition. However, it will also be recognized by one skilled in the art that, as long as the unknown samples and ouabain standard are assayed under substantially the same conditions, the method of this invention can be practiced in all of its aspects.

Ouabain used in the ouabain standard is commercially available from, for example, Sigma Chemical Company (St. Louis, Mo.) Calbiochem (La Jolla, Calif.), Aldrich (Milwaukee, Wis.).

Alternative, the ouabain used in the ouabain standard can be prepared as described by Schwartze, E. W. et al, *J. Pharmacol. Exp. Therap.*, 36:481–491 (1929).

When determining salt-sensitivity, diagnosing adenomas and endocrine cell hyperplasias or monitoring therapy, a suitable time interval for measuring levels of human ouabain in body fluids or tissue samples may be daily or weekly or any other suitable interval. A daily interval may be preferable for determining salt-sensitivity or diagnosing adenomas and endocrine cell hyperplasias because changes in the level of human ouabain in the subject in response to changes in dietary salt intake are believed, in the present invention, to be very rapid. On the other hand, a weekly interval may be preferable for monitoring changes in the level of human ouabain in the subject in response to pharmacologic therapy because changes in the level of human ouabain in the subject in response to pharmacologic therapy are believed, in the present invention, to be relatively slow.

As used herein, "hypertension therapy" includes the use of a low-salt diet, a diuretic, and the use of other pharmacological and non-pharmacological treatments, such as exercise, cessation of smoking, cessation of alcohol intake, and administration of an $\alpha$-blocker, a $\beta$-blocker or other sympatholytic agent, a converting enzyme inhibitor, a calcium channel blocker, or a combination thereof. These therapies are well known in the art (Kaplan, N., *Clin. Hyperten.*, 4th Ed., William & William, Baltimore, pp. 147–272 (1986)).

As used herein, "congestive cardiomyopathy therapy" includes the use of a low-salt diet, and administration of a diuretic agent, a cardiotonic steroid, such as digoxin, a vasodilator, a converting enzyme inhibitor, a phosphodiesterase inhibitor, or a combination thereof. These therapies are well known in the art (Braunwald, E., In: *Harrison's Principles of Internal Medicine,* 9th Ed., eds. Isselbacher, K. J. et al, McGraw-Hill, New York, pp. 1040–1044 (1980)).

As used herein, "renal failure therapy" includes the use of dietary potassium restriction, dietary protein restriction and dialysis. These therapies are well known in the art (Braunwald, E., In: *Harrison's Principles of Internal Medicine,* 9th Ed., eds. Isselbacher, K. J. et al, McGraw-Hill, New York, pp. 1040–1044 (1980); and Brenner, B. M., In: *Harrison's Principles of Internal Medicine,* 9th Ed., eds. Isselbacher, K. J. et al, McGraw-Hill, New York, pp. 1305–1306 (1980)).

As used herein, "adenoma or endocrine cell hyperplasia therapy" includes the use of spironolactone or surgery.

These therapies are well known in the art (Williams, G. H. et al, In: *Harrison's Principles of Internal Medicine,* 9th Ed., eds. Isselbacher, K. J. et al, McGraw-Hill, New York, pp. 1723–1726 (1980); and Kohler, P. O., In: *Harrison's Principles of Internal Medicine,* 9th Ed., eds. Isselbacher, K. J. et al, McGraw-Hill, New York, pp. 1679–1680 (1980)).

In a method for treating hypertension of the present invention, the antibody having binding specificity for ouabain is administered to the subject to as to bring about passive immunity. In this method, a subject that has an elevated level of ouabain is administered antibodies which have binding specificity for ouabain. These antibodies will bind to free human ouabain in the body fluid, and thus prevent inhibition of $(Na^++K^+)ATPase$ by human ouabain, resulting in a lowering of blood pressure.

The amount of antibody to administer will vary depending upon the age, weight and sex of the subject. Generally, the dosage to be administered is in the range of about 0.5 to 20 $\mu$g of antibody per kg of body weight, preferably about 2.0 to 3.0 $\mu$g of antibody per kg of body weight.

The antibody will generally be administered intravenously as a slow infusion, except in situations where blood pressure is elevated to a life-threatening level. Under such emergency conditions, rapid intravenous injections may be given.

The method of antibody production described herein can also be used to produce active immunity in subjects with ouabain-dependent hypertension. Such subjects would be immunized using, e.g., Conjugates 1, 2 and 3 described in Example 2 below.

More specifically, an emulsion containing about 1.0 to 30 mg of any one of Conjugates 1, 2 or 3 in 0.5 ml saline and 0.5 ml of Freund's complete adjuvant would be injected subcutaneously into the upper arm. About 4 to 6 weeks after the initial immunization, a boost consisting of about 1.0 to 30 mg of any one of the remaining Conjugates in 0.5 ml saline and 0.5 ml Freund's incomplete adjuvant would be injected subcutaneously in the upper arm. Then, an optional boost consisting of about 1.0 to 30 mg of the remaining Conjugate in 0.5 ml saline and 0.5 ml Freund's incomplete adjuvant would be injected subcutaneously in the upper arm about 4 to 6 weeks later. Then, optionally, a final boost consisting of about 1.0 to 30 mg of any one of Conjugates 1, 2 or 3 in 0.5 ml saline and 0.5 ml Freund's incomplete adjuvant would be injected subcutaneously in the upper arm about 4 to 6 weeks later.

The nature of the combined carrier-linking agent is unique to Conjugates 1–3 so as to ensure that the antisera response will be directed against ouabain and not the carrier or linking agent. That is, the carrier and linking agent vary among Conjugates 1–3. The use of a combination of different conjugates (containing different carriers and linking agents) is important for preparing antibodies having binding specificity for ouabain. However, it is not critical to specifically use Conjugates 1–3. Other conjugates (containing other carriers and/or linking agents) can be readily developed by one skilled in the art, and when employed in combination, used to prepare antibodies having binding specificity for ouabain.

The carriers and linking agents employed are not critical to the present invention (Hurn, B. A. L. et al, *Methods Enzymol.,* 70:104–142 (1980); Naegele, W. et al, In: *Radioimmunoassay of Steroid Hormones,* 2nd Ed., ed. Gupta, D., Verlag Chemie, Weinheim (Fed. Rep. Germany), pp. 55–72 (1980); and Chard, T., *An Introduction to Radioimmunoassay and Related Techniques,* Elsevier, Amsterdam, pp. 93–97 (1987)). Examples of carriers which can be employed include BSA, ovalbumin, polylysine, thyroglobulin, keyhole limpet hemocyanin and equine serum albumin. Examples of linking agents which can be employed include any reagent which provides a free amine after linkage to the carrier such as any alkyl diamine, such as hexane diamine; any dihydrazide, such as succinyldihydrazide; or any amino acid-N-carboxyanhydride, such as alanine-N-carboxyanhydride.

In addition to their use in the assays described above, the antibodies described herein are useful either alone or when conjugated to a matrix for extraction and purification of human ouabain from body fluids and tissues.

The following examples are provided for illustrative purposes only and are in no way intended to limit the scope of the present invention.

In the examples below, all solutions were made up in glass-distilled water and the water referred to in the examples was glass-distilled.

EXAMPLE 1

Purification and Characterization of Human Ouabain

I. Purification of Human Ouabain

Approximately 85 liters of human plasma were obtained from 30 donors irrespective of age, sex and blood pressure and dialyzed at 23° C. for 24 hr against 3 volumes of 10 mM ammonium acetate (pH 6.8) (Hamlyn, J. M. et al, *J. Biol. Chem.,* 264:7395–7404 (1989)).

The resulting dialysate was split into 4 batches and applied to an Amberlite XAD-2 column (bed volume=3.5 liters) previously washed with 10 liters of water. The adsorbed materials were eluted with 1 volume of methanol and dried under vacuum at 50° C. The solids were combined into 2 batches, resuspended in water and fractionated by HPLC on a preparative-scale, $C_{18}$ reverse-phase column. The column was eluted with a 0–100% (v/v) acetonitrile gradient containing 1.0% (w/v) TFA over 180 min (Hamlyn, J. M. et al, *J. Biol. Chem.,* 264:7395–7404 (1989)).

Fractions from the column were assayed for inhibition of ouabain-sensitive $^{86}Rb$ uptake by washed human red blood cells obtained by venipuncture. This assay was used as an index of sodium transport activity (Hamlyn, J. M. et al, *J. Biol. Chem.,* 264:7395–7404 (1989)).

More specifically, freshly washed cells were incubated for 2 hr at 37° C. (16% final hematocrit) in a final volume of 150 $\mu$l of flux buffer comprising 150 mM NaCl, 2.0 mM RbCl containing tracer amounts of $^{86}Rb$ (DuPont—New England Nuclear), 1.0 mM $MgCl_2$, 1.0 mM $Na_2HPO_4$, 2.0 mM $CaCl_2$, 5.0 mM glucose and 20 mM HEPES-Tris (pH 7.4) (hereinafter "flux buffer"). Incubations were initiated by addition of column fractions to the cells. Aliquots were removed at various times and mixed with ice-cold flux buffer lacking $^{86}Rb$ to quench the reactions. The quenched reactions were applied to a silicone oil cushion (Hysol XF1792B, Dexter Corp., Olean, N.Y.) in microcentrifuge tubes and centrifuged at 800×g for 10 min at 4° C. The red cell pellet was cut from deep-frozen tubes and trapped $^{86}Rb$ was determined by $\gamma$-counting. Flux data were expressed as nmol of Rb uptake/$10^8$ cells. In each case, a value of $1.11\times10^{13}$ cells/liter was used to convert packed cell volumes to cell number for the flux data calculations. Ouabain-insensitive $^{86}Rb$ uptake was estimated in parallel experiments by inclusion of 1.0 mM ouabain in the flux buffer. Ouabain-sensitive $^{86}Rb$ uptake was taken as the total uptake minus that obtained in the presence of 1.0 mM ouabain. The fractions found to inhibit ouabain-sensitive $^{86}Rb$ uptake were then assayed for the ability to inhibit $(Na^++K^+)ATPase$.

More specifically, $(Na^++K^+)$ATPase was purified from the outer medulla of dog kidney using the angle rotor procedure (Jorgensen, P. L., *Biochim. Biophys. Acta*, 356:36–52 (1974)) and stored frozen at −60° C. at 1.0 mg/ml in 25 mM imidazole-HCl (pH 7.5) and 1.0 mM EDTA, in small aliquots. $(Na^++K^+)$ATPase activity was determined at 37° C. from rate measurements in 1.0 ml of coupled optical assay mixture comprising 20 mM KCl, 100 mM NaCl, 4.5 mM $MgSO_4$, 5.0 mM EGTA, 3.0 mM ATP-$Na_2$, 1.2 mM phosphoenol-pyruvate-tricyclohexylammonium, 0.3 mM NADH, 100 MM TES-Tris (pH 7.4), 5.0 units of lactate dehydrogenase, and 5.0 units of pyruvate kinase (Hamlyn, J. M. et al, *Nature*, 300:650–652 (1982)). $(Na^++K^+)$ATPase activity was 99% ouabain-inhibitable with activities of 10–18 μmol/min/mg of membrane protein. Maximally effective concentrations of digitalis-like activity had no effect on the enzymatic components of the coupled optical assay as determined by inspection of rates in response to addition of 20–50 μM ADP. The maximal capacity of the coupled optical assay was at least 500–2000 fold greater than the typical maximal hydrolytic rate of the $(Na^++K^+)$ATPase and was not rate limiting under any assay condition described herein.

The protein concentration was estimated by dye binding (Bradford, N. M., *Anal. Biochem.*, 72:248–254 (1976)) using dried BSA as standard.

$(Na^++K^+)$ATPase inhibitory material eluting between 84 and 88 min (approximately 20% (v/v) acetonitrile) was combined to form a single fraction and then subjected to affinity extraction with partially purified lamb kidney $(Na^++K^+)$ATPase (Lane, L. K. et al, *Prep. Biochem.*, 9:157–170 (1979)).

More specifically, the single fraction was incubated for 3 hr at 37° C. in Tris buffer comprising 200 mM Tris-HCl (pH 7.2), 5.0 mM $MgCl_2$ and 5.0 mM $NaH_2PO_4/Na_2HPO_4$ (hereinafter "Tris buffer") to which an approximate 2-fold molar excess of $(Na^++K^+)$ATPase was added. Under these conditions, a variety of cardenolides bind with high affinity to $(Na^++K^+)$ATPase. Following incubation, the reaction mixture was centrifuged at 150,000×g for 2 hr at 4° C. to separate enzyme and enzyme-inhibitor complexes from soluble, unbound substances. The pellet was washed twice with Tris buffer, and recentrifuged as described above. Then, the pellet was resuspended in buffer comprising 2.0 mM Tris-HCl (pH 7.2) and 5.0 mM EDTA-Tris, and incubated for 6 hr at 37° C. to induce dissociation of enzyme-inhibitor complexes. Next, the enzyme was pelleted by centrifugation as described above and the supernatant was lyophilized. The lyophilized solids were taken up in water and, after filtration through a 5.0 μm filter (Acrodisc, Gelman Sciences Inc., Ann Arbor, Mich.), subjected to 2 sequential HPLC steps: (1) a Waters semi-preparative phenyl column (Milipore Corp., Milford, Mass.), eluted with a 0 to 10% (v/v) isopropanol gradient over a period of 0 to 5 min, and then eluted with a 10 to 30% (v/v) isopropanol gradient over a period of 5 to 55 min; and (2) a Beckman semi-preparative $C_{18}$ column (Beckman, Palo Alto, Calif.), eluted with a 0 to 10% (v/v) acetonitrile gradient over a period of from 0 to 5 min, and then eluted with a 10 to 30% (v/v) acetonitrile gradient over a period of 5 to 55 min.

A single peak of $(Na^++K^+)$ATPase inhibiting material, corresponding to 12 μg of human ouabain, was associated with a narrow symmetrical UV absorbing peak with no leading or trailing edges. 50 ml of plasma equivalents from the UV peak at 32 min inhibited ouabain-sensitive $^{86}$Rb uptake by 80% with no effect on ouabain-insensitive uptake.

The overall purification was calculated to be $>10^{10}$-fold with respect to the starting plasma (dry weight). The minimum calculated plasma concentration of human ouabain in the donor plasma was 321 pM after correction for losses in dialysis (25%). Chromatographic losses were not determined.

II. Structural Characterization of Human ouabain

Purified human ouabain was analyzed by fast atom bombardment mass spectrometry (FAB MS) using a VG 70 SE double focusing mass spectrometer (VG Instruments, Manchester, England).

More specifically, FAB spectra of the biologically active fraction and the two adjacent fractions (dissolved in a glycerol/thioglycerol matrix) from the final purification step of Section I. above were acquired over a mass range of m/z 100 to m/z 2500 Daltons. A unique protonated molecular ion at m/z 585 was observed in the active fraction. An accurate mass of 585.295 Daltons for human ouabain was determined in subsequent FAB MS by peak matching the m/z 585 peak with glycerol cluster ions. Based upon this determination, an elemental composition of $C_{29}H_{45}O_{12}$ was predicted for human ouabain. This composition matches that for ouabain (calculated accurate mass 585.291 for the protonated species). Additional experiments, using linked scan MS/MS were used to analyze the daughter ion fragment of the m/z 585 peak for human ouabain and ouabain. Both spectra were identical and showed a major ion at m/z 439 corresponding to the aglycone of ouabain. Thus, the sugar moiety of human ouabain, like that of ouabain, is a deoxyhexose.

Subsequently, acetylated derivatives of human ouabain and ouabain were examined by FAB MS.

FAB spectra of acetylated ouabain and human ouabain was carried out as follows:

FAB spectra were acquired over the mass range of from m/z 100 to m/z 1500 using a VG 70 SE mass spectrometer equipped with a Cs ion gun. Samples of ouabain and human ouabain were acetylated with 50 μl of acetic anhydride/15 mg/ml of dimethyl aminopyridine (DMAP) in pyridine (1:1) for 2 hr at room temperature. After excess reagent was removed under vacuum, the samples were dissolved in 0.5 μl of glycerol/thioglycerol (1:1).

After acetylation, the protonated molecular ions at m/z 585 disappeared and several new ions at higher masses were present. The new peaks were interpreted as follows: m/z 958, [584]+6 acetyl group (Ac)+$Na^+$; m/z 901, [584]+7 Ac+$Na^+$; m/z 959, [584] 6 Ac+DMAP+$H^+$; m/z 1001, [584] +7 Ac+DMAP+$H^+$; m/z 1043, [584]+8 Ac+DMAP+$H^+$. Magnetic field/electric field linked scan mass spectra of the m/z 535 parent ions of human ouabain shows a protonated ion at m/z 495.1, which is absent in the spectra of plant ouabain.

The resultant spectra for human ouabain and ouabain are identical. Both show abundant ions corresponding to the addition of six acetyl groups and less abundant ions for species with 7 and 8 acetyl groups. These results are consistent with the structure of ouabain which has six primary and secondary OH groups and two hindered tertiary OH groups.

The structure of ouabain is shown below.

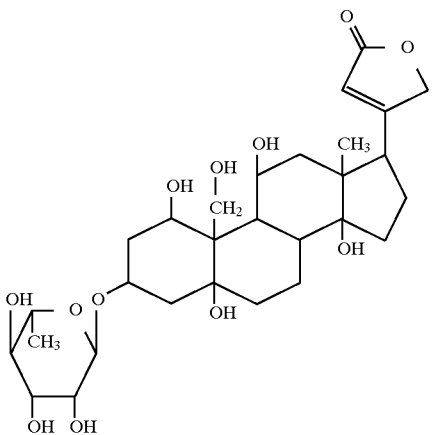

The accurate mass data, identical daughter ion and derivative spectra following acetylation suggest that human ouabain and ouabain are isomeric if not identical compounds.

III. Biological Characterization of Human Ouabain

Dose-response curves for human ouabain were generated for (1) inhibition of ouabain-sensitive uptake of $^{86}$Rb, (2) competition for $^3$H-ouabain binding, (3) inhibition of (Na$^+$+K$^+$)ATPase activity, and (4) competition for binding to antibodies having binding specificity for ouabain (Hamlyn, J. M. et al, *J. Biol. Chem.*, 264:7395–7404 (1989)).

A. Inhibition of Ouabain-sensitive Uptake of $^{86}$Rb

The inhibition of ouabain-sensitive uptake of $^{86}$Rb was carried out as described above. The calculated apparent $K_d$ value (and Hill coefficient) for human ouabain in this assay was 6.0 nM (–0.99).

B. Competition for $^3$H-ouabain Binding

Competition for $^3$H-ouabain (Amersham Corp. or DuPont—New England Nuclear) binding was carried out in 670 μl of binding buffer comprising, in final concentrations, 10 mM TES-Tris (pH 7.4), 0.5 mM EDTA, 5.0 mM MgCl$_2$ and 5.0 mM Na$_2$HPO$_4$ (hereinafter "binding buffer") and 50 nM ouabain containing $^3$H-ouabain tracer, and including the unknown sample. Binding was initiated by addition of 0.1–2 μg of purified (Na$^+$+K$^+$)ATPase and the reaction performed for 2 hr at 37° C. The reaction was quenched by addition of 2.0 ml aliquots of ice-cold binding buffer containing 100 μM unlabeled ouabain, followed by vacuum filtration over glass fiber filters (Whatman GF/B). Trapped $^3$H-ouabain was determined by scintillation counting, following 12 hr of soaking the filters in 4.0 ml of Beckman Ready Protein™ scintillation cocktail (Beckman, Palo Alto, Calif.). Nonspecific binding of $^3$H-ouabain was estimated by inclusion of excess unlabeled 100 μM ouabain in binding buffer and was always less than 2% of the total counts bound. All binding data were corrected for quench, and specific binding was expressed as pmol/mg of enzyme protein. Typical values of $^3$H-ouabain bound were 75–85 pmol/mg of enzyme protein as compared with phosphorylation levels of 100 pmol of acid stable $^{32}$P$_i$ incorporated/mg of enzyme protein. This corresponds to an overall ratio of 0.8 mol of ouabain bound/mol phosphorylation sites under type II conditions. The calculated apparent $K_d$ value (and Hill coefficient) for human ouabain in this assay was 7.7 nM (–0.97).

C. Inhibition of (Na$^+$+K$^+$)ATPase Activity

The inhibition of (Na$^+$+K$^+$)ATPase was carried out as described above. The calculated apparent $K_d$ value (and Hill coefficient) for human ouabain in this assay was 13.9 nM (–1.28).

D. Competition for Binding to Antibodies having Binding Specificity for Ouabain

The competition for binding to antibodies having binding specificity for ouabain was carried out by employing polyclonal antisera having titers >10,000 generated against ouabain in rabbits as described in Example 2 below. As discussed in detail in Example 2 below, the antisera showed no significant cross-reactivity (< about 0.02%) with the common steroids present in plasma. A competition ELISA was carried out as follows:

Microtiter plates were coated with 50 μl of a 1.0 ng/ml solution of Conjugate 4. Following washes with wash buffer comprising 0.9% (w/v) NaCl and 0.5% (v/v) Tween 20 (hereinafter "wash buffer"), residual sites were blocked with buffer comprising 136 mM NaCl, 1.46 mM KH$_2$PO$_4$, 0.8 mM Na$_2$HPO$_4$, 0.028 mM thimerosal, 0.5% (v/v) Tween 20, and 1.0% (w/v) BSA (pH 7.4). Known amounts of free ouabain or unknown samples were introduced followed by the addition of ouabain antisera at an overall dilution of 1:2×10$^6$. Incubations at 23° C. for 1 hr were terminated by repeated washing with wash buffer. Subsequently, a second incubation at 23° C. for 1 hr was performed with a 1:10$^3$ dilution of goat anti-rabbit IgG-peroxidase conjugate (Boehringer Mannheim, Indianapolis, Ind.). Following extensive washing with wash buffer, equal parts of 3,3',5,5'-tetramethylbenzidine and hydrogen peroxide (Kirkegaard and Perry, Gaithersburg, Md.) were added and incubated at 23° C. for 15 min. Color development was terminated by addition of 1.0M H$_3$PO$_4$ and read at 450 nm with a plate reader. Addition of 0.05 to 0.08 pmol of ouabain per well resulted in 50% displacement of bound ouabain. Each data point is the mean ±S.E.M. All lines were fitted by nonlinear regression to a sigmoidal function. The calculated apparent $K_d$ value (and Hill coefficient) for human ouabain in this assay was 1.6 nM (–0.65).

Inotropic properties of human ouabain were determined in left atria from 250 to 300 g guinea pigs mounted in 1.3 ml tissue chambers, between two pairs of platinum hooks; one hook served as an anchor and stimulating electrode and the other hook was connected to a force transducer. Atria were incubated at 37° C. in phosphate buffered saline comprising 130 mM NaCl, 5.4 g KCl, 1.8 mM MgCl$_2$, 0.4 mM NaH$_2$PO$_4$, 19 mM NaHCO$_3$ and 5.4 g of glucose (pH 7.3–7.4), and gassed with 95% O$_2$/5% CO$_2$. Tissues were stimulated at 1 Hz with twice threshold square pulses (0.8 to 1.0 V) of 0.7 to 1.2 msec duration. Resting tension was optimized for maximum isometric force generation. Control records were obtained once the phasic force was stabilized. Purified human ouabain was added from a stock solution (5.0 μg/ml in water) to give final concentrations of 43 to 170 nM. Addition of human ouabain to the bath to give a final concentration of 85 nM caused an increase in peak force that reached a plateau in 34 min. Developed force increased further with 170 nM human ouabain to a value of 294±28% (N=3 experiments) above the control. The apparent half-time for washout of the inotropic response to human ouabain was approximately 5 min. For comparison, 200 nm plant ouabain evoked an inotropic response of 311±41% (N=4 experiments) which returned to normal with a half-time of approximately 5 min upon washout.

Vasoactive properties of human ouabain were determined in rings of aorta from 250 to 300 g guinea pigs mounted in 1.3 ml tissue chambers, between two pairs of platinum hooks; one hook served as the anchor and the other hook was connected to a force transducer. The aortic rings were incubated at 37° C. in phosphate buffered saline. The rings were submaximally contracted for 3 to 7 min, every 35 min, with 0.2 or 1.0 μM histamine. Following three control contractions, the rings were exposed to 170 nM human ouabain for 30 minutes and then recontracted with 0.2 to 1.0 μM histamine. Human ouabain had no effect on baseline tension, but increased the histamine-evoked tension to 150±14% of control (N=4 experiments).

The apparent half-time for washout of the augmented tension response in the presence of human ouabain was much greater than 60 min. For comparison, 200 nM plant ouabain also did not affect baseline tension, but increased the histamine-evoked tension to 146±16% of control (N=4 experiments). The apparent half-time for washout of the augmented tension response in the presence of plant ouabain was also much greater than 60 min.

EXAMPLE 2

Preparation of Anti-Ouabain Antibodies

I. Preparation of Conjugates

Four different conjugates were prepared. Conjugates 1–3 were used for immunization of New Zealand White rabbits so as to prepare antibodies that bind specifically to ouabain. Conjugate 4 (containing BSA), rather than Conjugates 1–3, was used for the ELISA described in both Example 1 above, and Example 3 below, to ensure that the antisera would only recognize the ouabain portion of the conjugate.

Conjugate 1 was ovalbumin linked to ouabain using hexane diamine as a spacer. This conjugate was prepared in the following manner:

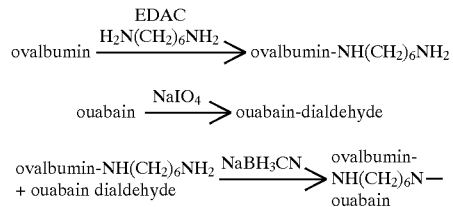

More specifically, to 2.4 g of hexane diamine free base (20.6 mmol) dissolved in 10 ml water was added 0.53 g of $K_2HPO_4$ (2.3 mmol) and the pH of the solution was adjusted to about 6.0 by the addition of 3.0 ml of concentrated aqueous HCl. Then, 350 mg of ovalbumin (Sigma A5503 Grade V) was added and dissolved to provide a clear, homogeneous solution. Next, 1.0 g of 1-(3-dimethylaminopropyl)-3-ethyl carbodiimide hydrochloride (EDAC) (5.22 mmol) was added in a single portion and the solution stirred at 15° C. for 24 hr. Qualitative measurement of the pH indicated little change during the course of the reaction. The resulting solution was dialyzed exhaustively against numerous changes of water and lastly against phosphate buffer comprising 1.8 mM $K_2HPO_4$ and 63 mM $KH_2PO_4$ (pH 5.0) (hereinafter "phosphate buffer"). A final volume of 25 ml was obtained. The major portion of this (18 ml) was lyophilized for storage, while the remainder (7.0 ml) was carried forward to the ouabain coupling.

0.5 g of ouabain octahydrate (0.68 mmol) was dissolved in 4.0 ml of water and 2.0 ml of acetone by gentle warming. At ambient temperature, 0.235 g of $NaIO_4$ (1.1 mmol) was added in a single portion. A precipitate accumulated during this reaction. After 2.5 hr, 1.22 g of $K_2HPO_4$. (5.0 mmol) was added and the reaction was stirred overnight. Then, 85 mg of meso-erythritol (0.65 mmol) was added; the reaction left an additional 60 min; and the acetone removed on a rotary evaporator. The residue was taken up in a small quantity of water and added to the above-described 7.0 ml ovalbumin solution. After stirring at 0° C. for 90 min, 82 mg of solid $NaBH_3CN$ (1.30 mmol) was added; then 52 mg of solid $NaBH_3CN$ (0.82 mmol) was added after 2.5 hr; and finally 50 mg of solid $NaBH_3CN$ (0.80 mmol) was added after 5 hr, with the reaction being maintained at 0° C. throughout. The reaction mixture acquired a cloudy appearance at this time. It was left at 4° C. for three days, with the appearance of significant quantities of precipitate. The entire reaction mixture was dialyzed exhaustively against 65 mM potassium phosphate buffer (pH 6.0), concentrated by lyophilization, and then resuspended in 5.0 ml of water and gently stirred for 2 hr. The precipitate was separated by centrifugation at 1000×g and the soluble protein passed through a φ4.0 cm×23 cm Sephadex G-25 (20–50 μm) column. The protein fractions were combined, dialyzed against 10 mM NaCl, and 0.8 μm filtered to provide 27 ml of solution containing Conjugate 1.

Conjugate 2 was poly-D-lysine linked directly to ouabain. This conjugate was prepared in the following manner:

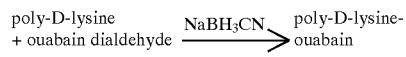

More specifically, 300 mg of ouabain-octahydrate (0.41 mmol) was dissolved in 3.0 ml water and 2.0 ml acetone by gentle warming. After cooling to ambient temperature, 0.215 g of $NaIO_4$ was added with the rapid formation of a precipitate. During a 5 hr period, 225 mg of $K_2HPO_4$ was added portionwise (1.0 mmol total). The reaction was then quenched with 25 mg of meso-erythritol (0.20 mmol) and left at ambient temperature overnight. The acetone was removed on a rotary evaporator and the residue taken up in several small volumes of water, total volume 4.0 ml. 1.75 ml of this solution was then added to a solution of 36 mg of poly-D-lysine (Sigma P7886: DP 254, $M_r$=53,000 (vis): DP=236, $M_4$=49,000 (lalls)) in 1.0 ml of citrate-phosphate buffer comprising 30 mg of citric acid and 50 mg of $K_2HPO_4$. A final adjustment of the reaction pH to about 5.0–5.5 was made by the addition of 0.10 ml of 1.0M citric acid. The clear, colorless solution was kept at 0° C. for 4.5 hr and then placed at 10° C. overnight. During this time, the reaction acquired a dark yellow-brown color which was discharged instantly by the addition of a 0.1 ml of a 1.72M solution of $NaBH_3CN$. After 7 hr at 10° C., a faint yellow color appeared; this too was discharged by the addition of 0.10 ml of a 1.61M solution of $NaBH_3CN$ and the reaction once again kept overnight. The reaction mixture remained colorless and contained a small quantity of precipitate. It was dialyzed exhaustively against water at ambient temperature; concentrated by lyophilization; resuspended with 2.5 ml of water, centrifuged at 1000×g, and the supernatant passed through a φ4.0 cm×25 cm Sephadex G-25 (20–50 μm) column. The polypeptide-containing fractions were combined and dialyzed against water. After filtration to remove insoluble material, 6.0 ml of solution of Conjugate 2 was obtained.

Conjugate 3 was ovalbumin linked to ouabain using succinyl dihydrazide as a spacer. This conjugate was prepared in the following manner:

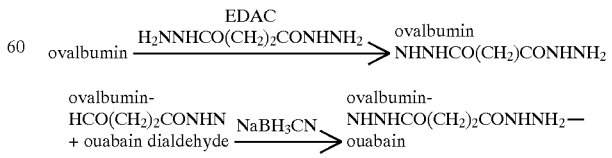

More specifically, 1.0 g of succinyldihydrazide (Aldrich S550-2; 6.8 mmol) was dissolved with heating in 14 ml of water. Most, but not all, of the solid remained in solution upon cooling. To this solution was added 0.40 g of KH$_2$PO$_4$ and the pH was adjusted to about 5.0 with 0.1 ml of concentrated aqueous HCl. 215 mg of chicken egg ovalbumin and then 0.67 g of 1-(3-dimethylaminopropyl)-3-ethyl carbodiimide hydrochloride (3.5 mmol) were added to yield a mostly homogeneous solution. After 20 hr at ambient temperature the solution, without precipitate, was exhaustively dialyzed against water and then finally against acetate buffer comprising 2.65 g of CH$_3$CO$_2$Na and 0.70 ml of CH$_3$CO$_2$H in 500 ml of water (pH about 4.5).

Separately, 375 mg of ouabain octahydrate (0.41 mmol) was dissolved in 3.0 ml of water and 2.0 ml of acetone by warming. After cooling, 295 mg of NaIO$_4$ was added. One half hour later, the reaction mixture was neutralized with 1.0 mmol of CH$_3$CO$_2$Na and stirred overnight. Meso-erythritol (1.0 mmol) was added as a quench and the acetone removed on a rotary evaporator.

The oxidized ouabain was then added to the ovalbumin at ambient temperature for 4 hr, and then at 10° C. for 60 hr. No precipitate appeared. After dialysis, the protein was concentrated by lyophilization, resuspended in water, and purified by G-25 chromatography. The protein fractions were combined and further dialyzed against water. After removing a small portion for UV spectral analysis, the remainder of Conjugate 3 was lyophilized.

Conjugate4 was BSA linked to ouabain using hexane diamine as a spacer. This conjugate was prepared in the following manner:

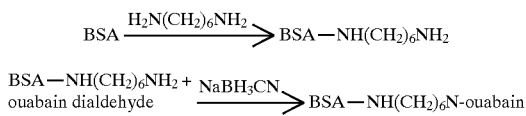

More specifically, 3.5 g of hexane diamine free base (30 mmol) was dissolved in 20 ml of water and the pH adjusted to about 8.0 by the addition of 11.0 g of solid KH$_2$PO$_4$ (81 mmol). To this clear, light yellow-colored solution was added 520 mg of BSA (Sigma A7888 RIA grade, about 7.4 µmol) and the protein dissolved by gentle stirring to provide a slightly turbid solution. In a single portion was added 1.0 g of 1-(3-dimethylaminopropyl)-3-ethyl carbodiimide hydrochloride (5.2 mmol) and the reaction was stirred for 20 hr at ambient temperature. The reaction was then dialyzed against multiple changes of water and finally against 2.0 liters of water containing 8.0 g of KH$_2$PO$_4$ (58.8 mmol) The protein solution was divided into two equal portions. The first was taken to dryness and the protein stored as the powder. The second was concentrated to a volume of about 15 ml by lyophilization and reacted with the oxidized ouabain as described below.

0.67 g of ouabain octahydrate (0.91 mmol) was dissolved in 4.0 ml of acetone and 4.0 ml of water with gentle warming. To this was added, at ambient temperature, 0.35 g of NaIO$_4$ (1.7 mmol). Observation of a precipitate was made within 5 min of the addition; copious solid was evident within 20 min. An additional 2.0 ml of water was added, with some dissolution of the precipitate, and the reaction was stirred overnight. Then, 100 mg of meso-tartaric acid was added as a quench and the acetone removed with a rotary evaporator. The precipitate dissolved during this concentration but upon brief standing at 5° C. reappeared. The pH of the oxidized ouabain solution was adjusted to about 4.0 with solid K$_2$HPO$_4$, combined with the second albumin portion (from above) to give a total volume of 25 ml, and a final adjustment of the pH to about 6.0 made with additional K$_2$HPO$_4$. The reagents were stirred together for 30 min and then 70 mg of NaBH$_3$CN (1.1 mmol) added; followed by adding 170 mg of NaBH$_3$CN (2.7 mmol) 90 min later. After 17 hr, the reaction mixture was briefly dialyzed against 25 mM Tris buffer (pH 7.9); concentrated by lyophilization; and applied to a φ3.0 cm×36 cm Sephadex G-25 (20–50 µm) column. The protein fractions containing Conjugate 4 eluted well separated from the oxidized ouabain, and after overnight dialysis against 25 mM Tris buffer (pH 7.9), were examined by UV difference spectroscopy.

II. Immunization and Collection of Antisera

Antibodies which specifically bind to ouabain were prepared as follows:

9New Zealand White rabbits were immunized using 1.0 mg/ml of Conjugate 1 dissolved in an emulsion comprising 0.5 ml of saline and 0.5 ml of complete Freunds adjuvant. This emulsion was injected intradermally at ten sites distributed along each side of the spinal column on the shaved back of the rabbits using 0.1 ml of emulsion per site.

Four weeks after the first immunization, the rabbits were boosted by administering 1.0 mg/ml of Conjugate 2 dissolved in an emulsion comprising 0.5 ml of saline and 0.5 ml of incomplete Freunds adjuvant. This emulsion was injected intradermally at ten sites distributed along each side of the spinal column on the shaved back of the rabbits using 0.1 ml of emulsion per site.

Four weeks after the second immunization, the rabbits were boosted by administering 1.0 mg/ml of Conjugate 3 dissolved in an emulsion comprising 0.5 ml of saline and 0.5 ml of incomplete Freunds adjuvant. This emulsion was injected intradermally ten times at five sites along each side of the spinal column on the shaved back of the rabbits using 0.1 ml of emulsion per site.

In each immunization, the conjugates shared a common ouabain moiety while the carrier protein or spacer group used to link ouabain to the carrier was varied. This protocol was designed to make ouabain the emphasis of the antigenic response and to de-emphasize any response to the carrier protein or spacer group used.

Polyclonal anti-ouabain antisera was obtained from the immunized rabbits by collecting blood from the central ear artery, allowing the blood to clot for 2 hr at room temperature, centrifuging the clotted blood at 1000×g for 10 min, and removing the polyclonal anti-ouabain antisera.

The polyclonal antisera was extensively characterized by testing the degree to which it cross-reacted with (1) other substances known to be present in human body fluids and tissues, and (2) cardiotonic steroids closely related to ouabain but not known to be present in human body fluids and tissues. These substances and their cross-reactivities (relative to ouabain) are set forth in Table 1 below.

TABLE 1

| Substances Known to Be Present in Human Body Fluids and Tissues | |
|---|---|
| Aldosterone | 0.012% |
| Atrial natriuretic peptide | None detected |
| Angiotensin I | None detected |
| Angiotensin II | None detected |
| Arginine vasopressin | None detected |
| β-estradiol | None detected |
| Chlormadinone acetate | None detected |
| Cholesterol | None detected |
| Citrate | None detected |
| Corticosterone | 0.0035% |
| Deoxycorticosterone | 0.0046% |

TABLE 1-continued

| | |
|---|---|
| Dehydroisoandrosterone | None detected |
| Dehydroisoandrosterone-3-sulfate | None detected |
| Hydrocortisone | None detected |
| Progesterone | 0.0011% |
| Renin | None detected |
| Taurocholic acid | None detected |
| Testosterone | 0.0042% |

| Cardiotonic Steroids Not Known to be Present in Human Body Fluids and Tissues | |
|---|---|
| Digoxin | 5.2% |
| Digitoxin | 28% |
| Dihydroouabain | 0.16% |
| Lanatoside C | 2.49% |
| Ouabagenin | 40% |
| Strophanthidin | 66% |

It is apparent from the results shown in Table 1 above that this antisera is highly specific for ouabain and other closely related cardiotonic steroids, such as digitoxin, ouabagenin and strophanthidin. None of the compounds present in human body fluids or tissues cross-reacted significantly. The dissociation constant of the antibodies is in the range of 2.0 to 4.0 nM of ouabain and is thus of high affinity.

EXAMPLE 3

Immunological Assay

I. Enrichment of Samples

In order to effect enrichment of the plasma, the plasma sample was diluted at least 1:5 (w/v or v/v) with 0.1% (w/v) TFA in water. Then, the diluted sample was passed through a 0.5 g Analytichem International $C_{18}$ column which had previously been wetted with 5.0 ml of 100% (v/v) acetonitrile, followed by washing with 10 ml of water. Once the sample was applied to the column, the column was washed twice with 3.0 ml of water to remove any materials which did not bind. A single fraction was eluted and collected by washing the column with 3.0 ml of 25% (v/v) acetonitrile. This fraction was dried and redissolved in assay buffer. The resulting solution was used for determination of plasma levels of human ouabain as described below.

II. Assay of Samples

The anti-ouabain antisera obtained in Example 2 was utilized in a competition ELISA to measure plasma levels of human ouabain using ouabain as a standard as described below.

A. Preparation of Support 96-well EIA microtiter plates (Costar, Mass.) were coated with Conjugate 4 by adding 50 μl of a solution containing 50 pg of Conjugate 4 dissolved in 0.05M carbonate-bicarbonate buffer (pH 9.6), and incubated overnight at 4° C. After incubation, any Conjugate 4 which had not adhered to the microtiter plate was removed by washing the wells 3 times with 200 μl/well of rinse solution comprising 0.05% (v/v) Tween 20 and 150 mM NaCl (hereinafter "rinse solution"). This removed the excess unbound Conjugate 4 leaving only that bound to the EIA plate.

The remaining non-specific binding sites in each well on the plates were blocked by adding 100 μl of assay buffer to each well and incubating the resulting microtiter plates at room temperature for at least 1 hr or at 4° C. for at least overnight. Then, the assay buffer was removed by washing the wells with 200 μl/well of rinse solution.

B. Preparation of Standard

A ouabain standard curve was prepared by adding 25 μl of different concentrations of ouabain (Sigma) dissolved in assay buffer, ranging from 0.025 pmole/25 μl to 12.8 pmole/25 μl, to different wells of the microtiter plate.

C. Unknown Sample

The level of human ouabain in the unknown sample was measured by adding 25 μl of different dilutions of an unknown sample to different wells of the microtiter plate.

D. Initiating Assay

A competition ELISA was initiated by adding 25 μl of anti-ouabain antisera (diluted 1:30,000 or more with assay buffer) to each well and incubating for 1 hr in a shaking bath at room temperature.

The anti-ouabain antibody recognizes both the ouabain portion of Conjugate 4 (attached to the microtiter plate) as well as the ouabain standard and human ouabain. The amount of anti-ouabain antibody that binds to Conjugate 4 which is bound to the microtiter plate is inversely proportional to the amount of ouabain standard or human ouabain.

E. Development of Assay

After 1 hr of incubation, each well was washed 3 times with 200 μl of rinse solution. Into each well was added 50 μl of goat anti-rabbit IgG antibody-peroxidase conjugate (Boehringer Mannheim Biochemicals) diluted 1:1000 with assay buffer. The microtiter plates were then incubated in a shaking bath with this second antibody for 1 hr at room temperature.

The second incubation step allows the anti-IgG antibody to bind to the rabbit anti-ouabain antibody which is bound to the well on the microtiter plate. Therefore, the amount of goat anti-rabbit IgG which will bind is directly proportional to the amount of rabbit anti-ouabain antibody which was bound in the first incubation. After this second incubation, each well was washed 4 times with 200 μl of rinse solution to remove any free goat anti-rabbit IgG antibody-peroxidase conjugate.

The amount of anti-rabbit IgG antibody-peroxidase conjugate remaining bound in each well was measured by adding 50 μl of a peroxidase substrate consisting of 1 part Kirkegaard and Perry (Gaithersburg, Md.) 3,3',5,5'-tetramethylbenzidine Solution A reagent and 1 part Kirkegaard and Perry hydrogen peroxide Solution B reagent. The microtiter plates were then shaken at room temperature and the resulting blue color was allowed to develop until an approximate absorbance of 0.75 O.D. units was obtained at 650 nm. At this point, the reaction was terminated by adding 50 μl of 1.0M $H_3PO_4$. The addition of $H_3PO_4$ causes an increase in color intensity and changes the reagent color from blue to yellow. Therefore, the OD was measured at 450 nm. The wells developing more color contained more goat anti-rabbit IgG antibody-peroxidase conjugate, and thus contained more rabbit anti-ouabain antibody. This means that they contained less ouabain standard or human ouabain in the original incubation mixture because the binding of anti-ouabain antibody to Conjugate 4 bound to the wells in each microtiter plate is inversely proportional to the ouabain standard or human ouabain concentration during the initial incubation of the competition ELISA. The wells developing less color contained little goat anti-rabbit IgG antibody-peroxidase conjugate. Therefore, they contained little rabbit anti-ouabain antibody. This means that these samples contained higher levels of ouabain or human ouabain in the original incubation mixture.

A standard curve was prepared by plotting observed $OD_{450}$ versus the known amount of ouabain added to the standard curve wells of the original incubation mixture. By comparing the $OD_{450}$ obtained for human ouabain samples with the amount of ouabain on the standard curve required to give the same OD, unknown human ouabain levels were determined.

This assay technique can be used to measure levels of human ouabain in a subject afflicted with pre-hypertension, hypertension (Example 4 below) and white-coat hypertension, in a subject at risk to develop renal failure (Example 4 below), in a subject at risk to develop congestive cardiomyopathy (Example 5 below), in salt-sensitive subjects, and in subjects afflicted with adenomas and endocrine cell hyperplasias. In all instances, except the congestive cardiomyopathy, elevated levels, i.e., above the normal range, of human ouabain are indicative of the aforementioned conditions. Levels of human ouabain are reduced in congestive cardiomyopathy and in otherwise normal individuals who are at risk for future development of cardiomyopathy.

EXAMPLE 4

Measurement of Ouabain Levels in Rats with Induced Renal Disease and Hypertension Three groups of rats were studied: (i) Normal 300 g Sprague Dawley male rats; (ii) 300 g Sprague Dawley male rats subjected to unilateral nephrectomy (removal of one kidney) and administered 0.9% (w/v) NaCl-drinking water for 2 weeks to simulate renal disease; and (iii) 300 g Sprague Dawley male unilateral nephrectomized rats administered 0.9% (w/v) NaCl-drinking water, and treated with a silastic implant impregnated with 100 mg/kg deoxycorticosterone acetate for 2 weeks to induce adrenocorticoid-induced hypertension. After 2 weeks of the appropriate treatment, the mean arterial blood pressure in each rat was measured by the tail cuff method (Cimini, C. M. et al, Lab. Animal Sci., 35:412–416 (1985); tail cuff purchased from IITC, Landing, N.J.). Trunk blood or venous blood was removed from unstressed rats and was collected in chilled tubes containing (in final concentrations) 2.8 mM $Na_2EDTA$, 3.4 mM $Na_2EGTA$ and 2.6 mM glutathione. The blood was continuously stirred to ensure uniform anticoagulation. Then, the blood was centrifuged at 8000 to 10,000×g for 10 min at room temperature. The plasma was removed in 5.0 ml aliquots and stored at $-20°$ to $-70°$ C. for up to 5 to 6 months. The fresh or thawed plasmas were enriched for ouabain as described in Example 3, Section I, and the resulting enriched samples were assayed for levels of ouabain using the ELISA described in Example 3, Section II. The results obtained are shown in Table 2 below.

TABLE 2

| Group | Mean Arterial Blood Pressure (mm Hg) | Ouabain Levels (pmol/liter) |
|---|---|---|
| Normal | 99.8 ± 1.5 (N = 6)* | 66 ± 6 (N = 8) |
| Renal Disease | 113 ± 4 (N = 6) | 105 ± 43 (N = 6) |
| Hypertension | 156 ± 12 (N = 5) | 975 ± 79 (N = 5) |

*Data are the means ± standard errors for N rats.

The results in Table 2 above demonstrate that rats with renal disease have elevated levels of ouabain with only a small increase in blood pressure, whereas hypertensive rats have elevated levels of ouabain and an increased blood pressure. These rat models for renal disease and hypertension, which are well-known to be correlatable to renal disease and hypertension in humans, demonstrate that levels of human ouabain can be employed to diagnose renal disease and hypertension in humans and to monitor therapies for renal disease and hypertension in humans.

EXAMPLE 5

Measurement of Ouabain Levels in Humans with Cardiomyopathy

Two groups of humans were studied: (i) normal subjects; and (ii) subjects with untreated left ventricular cardiomyopathy. Blood was removed from these subjects by venipuncture and collected in chilled tubes as described in Example 4. The plasmas were separated as described in Example 4 and then enriched for human ouabain as described in Example 3, Section I, and the resulting enriched samples were assayed for levels of human ouabain using the ELISA described in Example 3, Section II. The results obtained are shown in Table 3 below.

TABLE 3

| Group | Ouabain Levels (pmol/liter) |
|---|---|
| Normal | 53 ± 8 (N = 7)* |
| Cardiomyopathy | 24 ± 8 (N = 4) |

*Data are the means ± standard errors for N subjects.

The results in Table 3 above demonstrate that levels of human ouabain are reduced in patients with untreated cardiomyopathy and thus that the levels of human ouabain can be employed to determine subjects at risk to develop congestive cardiomyopathy and to monitor therapy for congestive cardiomyopathy.

While this invention has been described in detail and with reference to specific embodiments thereof, it will be apparent to one skilled in the art that various changes can be made therein without departing from the spirit and scope thereof.

We claim:

1. An antibody having binding specificity for human ouabain, wherein said antibody has a cross-reactivity for steroids present in human plasma on the order of about 1.0% or less cross-reactivity, wherein said antibody has a dissociation constant on the order of about 2.0 to 7.0 nM of plant ouabain.

2. The antibody as claimed in claim 1, wherein said antibody has a dissociation constant on the order of about 2.0 to 4.0 nM of plant ouabain.

3. The antibody as claimed in claim 2, wherein said antibody has a cross-reactivity for steroids present in human plasma on the order of about 0.02 to 0.001% cross-reactivity.

4. A substantially purified human ouabain/which is capable of being detected in an immunoassay by an antibody having binding specificity for human ouabain, wherein said antibody has a cross-reactivity for steroids present in human plasma on the order of about 1.0% or less cross-reactivity.

5. Substantially pure human ouabain, wherein said human ouabain shows a protonated ion at m/z 495.1 in magnetic field/electric field linked scan mass spectra of the m/z 535 parent ions, which protonated ion is absent in the spectra of plant ouabain.

6. Substantially pure human ouabain obtained from human body fluid or human tissue sample.

7. Substantially pure human ouabain, wherein said human ouabain is obtainable by the process comprising the steps of:

(A) dialyzing human plasma or serum to remove bulk proteins and collecting the resulting dialysate;

(B) separating charged molecules from uncharged polar molecules in the resulting dialysate obtained in step (A) so as to obtain fractions containing uncharged polar molecules;

(C) separating lipids from the resulting fractions containing uncharged polar molecules obtained in step (B) so as to obtain fractions which do not contain lipids;

(D) assaying the resulting fractions which do not contain lipids obtained in step (C) for inhibition of sodium transport activity;

(E) subjecting the resulting fractions obtained in step (D) which are found to inhibit sodium transport activity to $(Na^++K^+)$ATPase affinity extraction; and (F) subjecting the resulting compounds which are found to bind to $(Na^++K^+)$ATPase in step (E), to reverse-phase HPLC, so as to obtain human ouabain.

8. Substantially pure human ouabain, wherein said human ouabain is obtainable by the process comprising the steps of:

(A) homogenizing human tissue and removing bulk proteins therefrom and collecting the resulting homogenate;

(B) separating charged molecules from uncharged polar molecules in the resulting homogenate obtained in step (A) so as to obtain fractions containing uncharged polar molecules;

(C) separating lipids from the resulting fractions containing uncharged polar molecules obtained in step (B) so as to obtain fractions which do not contain lipids;

(D) assaying the resulting fractions which do not contain lipids obtained in step (C) for inhibition of sodium transport activity;

(E) subjecting the resulting fractions obtained in step (D) which are found to inhibit sodium transport activity to $(Na^++K^+)$ATPase affinity extraction; and (F) subjecting the resulting compounds which are found to bind to $(Na^++K^+)$ATPase in step (E), to reverse-phase HPLC, so as to obtain human ouabain.

9. A process for obtaining human ouabain comprising the steps of:

(A) dialyzing human plasma or serum to remove bulk proteins and collecting the resulting dialysate;

(B) separating charged molecules from uncharged polar molecules in the resulting dialysate obtained in step (A) so as to obtain fractions containing uncharged polar molecules;

(C) separating lipids from the resulting fractions containing uncharged polar molecules obtained in step (B) so as to obtain fractions which do not contain lipids;

(D) assaying the resulting fractions which do not contain lipids obtained in step (C) for inhibition of sodium transport activity;

(E) subjecting the resulting fractions obtained in Step (D) which are found to inhibit sodium transport activity to $(Na^++K^+)$ATPase affinity extraction; and (F) subjecting the resulting compounds which are found to bind to $(Na^++K^+)$ATPase in step (E), to reverse-phase HPLC, so as to obtain human ouabain.

10. A process for obtaining human ouabain comprising the steps of:

(A) homogenizing human tissue and removing bulk proteins therefrom and collecting the resulting homogenate;

(B) separating charged molecules from uncharged polar molecules in the resulting homogenate obtained in step (A) so as to obtain fractions containing uncharged polar molecules;

(C) separating lipids from the resulting fractions containing uncharged polar molecules obtained in step (B) so as to obtain fractions which do not contain lipids;

(D) assaying the resulting fractions which do not contain lipids obtained in step (C) for inhibition of sodium transport activity;

(E) subjecting the resulting fractions obtained in step (D) which are found to inhibit sodium transport activity to $(Na^++K^+)$ATPase affinity extraction; and (F) subjecting the resulting compounds which are found to bind to $(Na^++K^+)$ATPase in step (E), to reverse-phase HPLC, so as to obtain human ouabain.

* * * * *